(12) United States Patent
Tkachenko et al.

(10) Patent No.: US 9,498,166 B2
(45) Date of Patent: Nov. 22, 2016

(54) METHOD FOR DISPLAYING THE TEMPERATURE FIELD OF A BIOLOGICAL SUBJECT

(71) Applicant: Smart Thermograph PTE. LTD., Singapore (SG)

(72) Inventors: Yury Aleksandrovich Tkachenko, Nizhny Novgorod (RU);
(Continued)

(73) Assignee: Smart Thermograph PTE. Ltd., Singapore (SG)

( * ) Notice: Subject to any disclaimer, the term of this patent is extended or adjusted under 35 U.S.C. 154(b) by 50 days.

(21) Appl. No.: 13/771,996

(22) Filed: Feb. 20, 2013

(65) Prior Publication Data
US 2013/0165797 A1 Jun. 27, 2013

Related U.S. Application Data

(63) Continuation of application No. PCT/RU2011/000695, filed on Sep. 9, 2011.

(30) Foreign Application Priority Data

Nov. 2, 2010 (RU) ................ 2010144628

(51) Int. Cl.
*A61B 6/00* (2006.01)
*A61B 5/00* (2006.01)
(Continued)

(52) U.S. Cl.
CPC ............ *A61B 5/7425* (2013.01); *A61B 5/0075* (2013.01); *A61B 5/0077* (2013.01); *A61B 5/015* (2013.01);
(Continued)

(58) Field of Classification Search
USPC ......... 600/473–475; 382/128, 276, 278, 286, 382/287, 291, 294
See application file for complete search history.

(56) References Cited

U.S. PATENT DOCUMENTS 6,067,371 A * 5/2000 Gouge et al. ................. 382/128
6,440,084 B1 * 8/2002 Gentempo et al. ........... 600/549
(Continued)

FOREIGN PATENT DOCUMENTS

EP 1326063 7/2003
JP 2010194073 9/2010
(Continued)

OTHER PUBLICATIONS

DiRomualdo et al. Superimposition of thermal imaging to visual imaging using homography. Proceedings of the 29th Annual International Conference of the IEEE EMBS. Aug. 2007.*
(Continued)

*Primary Examiner* — James Kish
(74) *Attorney, Agent, or Firm* — Burns & Levinson LLP; Orlando Lopez

(57) ABSTRACT

Measurements for medical diagnostic purposes measure the temperature of parts of the body to diagnose illnesses and for monitoring dynamics of an illness during treatment. This increases accuracy and clarity and simplifies technical implementation. An image of the region of the body of a biological subject under investigation is input into a computer database, with the image being output to a monitor of the computer, wherein the measurement points for measuring the temperature in the region of the subject under investigation are displayed in the image of the subject on the monitor screen and, once the measurements have been taken and the results of the measurements have been processed in the computer, an image of the temperature field is generated by a computer.

8 Claims, 4 Drawing Sheets

(72) Inventors: Yuliya Pavlovna Potekhina, Nizhny Novgorod (RU); Igor Evgenievich Davydov, Samara (RU); Margarita Vladimirovna Golovanova, Nizhny Novgorod (RU); Roman Aleksandrovich Plokhov, Nizhny Novgorod (RU); Ivan Nikolaevich Lozgachev, Pavlovo (RU)

(51) Int. Cl.
*A61B 5/01* (2006.01)
*G01J 5/00* (2006.01)
*G01J 5/02* (2006.01)
*G01J 5/08* (2006.01)
*G06T 11/20* (2006.01)

(52) U.S. Cl.
CPC .............. *A61B 5/743* (2013.01); *G01J 5/0025* (2013.01); *G01J 5/025* (2013.01); *G01J 5/0846* (2013.01); *G01J 5/0859* (2013.01); *G06T 11/206* (2013.01); *G06T 2207/10048* (2013.01); *G06T 2207/30088* (2013.01)

(56) References Cited

U.S. PATENT DOCUMENTS

| 2003/0028114 | A1* | 2/2003 | Casscells et al. ............. 600/474 |
| 2003/0120171 | A1* | 6/2003 | Diamantopoulos et al. .. 600/549 |
| 2004/0021773 | A1* | 2/2004 | Hayakawa .................... 348/164 |
| 2008/0139931 | A1* | 6/2008 | Butz et al. .................... 600/427 |

FOREIGN PATENT DOCUMENTS

| RU | 37334 | 5/2004 |
| RU | 2007138079 | 4/2009 |

OTHER PUBLICATIONS

M. Glehr et al., Thermal Imaging as a Noninvasive Diagnostic Tool for Anterior Knee Pain Following Implantation of Artificial Knee Joints, Archiv Euromedica, 2012, vol. 3.
Gustov, A.V., Ozonoterapia en la neurologia: monografia, 3 edicion, corregida y aumentada, Nizhny Novgorod: Editorial de NGMA, 2011.
Arora N., Martins D., Ruggerio D., et al., Effectiveness of a noninvasive digital infrared thermal imaging system in the detection of breast cancer, American Journal of Surgery, 2008, 196, 523-526.
Parshikova S.A., Parshikov V.V., Potekhina Yu. P. Prognosis of complications by infrared thermography in treatment of children with facial bites; Bulletin of Experimental and Clinical Suraery V2. 2012.
Potekhina J.P., Gustov A.V., Gafiatullin I.A,, Golovanova M.V.; Capabilities of infrared thermometry and thermography in acute and chronic cerebral circulation disturbances: Russian Journal of Dentistry 2013.
Potekhina J.P.et al, Diagnostic and prognostic significance of the infrared thermography method for examination of patients suffering pathologic states, 2013.
Durnovo et al, Development and analysis of the peculiarities of the thermal maps of maxillofacial region depending on the age and sex, 2013.
Potekhina J.P., et al. Kosmetic International, 2012, Tom 11, No. 2.
Karelid, M. Image Enhancement over a Sequence of Images (2008), Master Thesis, Department of Electrical Engineering, Linköpings universitet, SE-581 83 Linköping, Sweden.
Prince, S.J.D. et al. Augmented Reality Camera Tracking with Homographies, IEEE Computer Graphics and Applications, Nov./Dec. 2002.
Brown, L.G. A Survey of Image Registration Techniques, ACM Computing Surveys, vol. 24, No. 4, Dec. 1992.
Williams, D.L. et al. Implementation of a Digital Image Superposition Algorithm for Radionuclide Images, J. Nucl. Med, vol. 19, No. 3 (1978).

\* cited by examiner

METHOD FOR DISPLAYING THE TEMPERATURE FIELD OF A BIOLOGICAL SUBJECT

CROSS-REFERENCE TO RELATED APPLICATIONS

This is a continuation of application PCT/RU2011/000695 filed Sep. 9, 2011 which is incorporated herein by reference, and which claims priority on Russian patent application 2010144628 filed Nov. 2, 2010, which priority claim is repeated here.

TECHNICAL FIELD

The present invention relates to medicine and veterinary medicine, namely, to the measurements for diagnostic purposes by measuring the temperature of the body parts; the invention can be used in medical and veterinary practice for diagnosis of diseases and for monitoring of the dynamics of the disease during the course of treatment.

In this application, the term "image of the object" and "image of the examined area of the object" includes: electronic image of received on photosensitive element of the photo camera, subsequent transfer of the electronic image to a personal computer in any conventional format, as well as an electronic model of a biological object with the image of the examined area in the format 2D or 3D.

PRIOR ART

It is widely known that a disease of organs of a biological object is accompanied by the change in temperature in the relevant to the disease areas of the body of the biological object. Information on the temperature field gives an indication of the presence of the pathology in the body of the biological object, herewith, diagnostics of the revealed pathology is performed based on known temperature signs.

Currently, expensive computer thermographs are used for the purpose of obtaining information about the temperature field of a person; thermographs register thermal (infrared) radiation from a person through infrared-sensitive sensor elements and display it on the computer screen in the form of a thermogram, which is the image of the thermal radiation of the person. However, due to the high cost and complexity of the service, not all medical facilities have thermographs, and for the same reasons, thermographs practically are not used in veterinary medicine.

These circumstances contribute to the development of methods that can display the temperature field of biological objects using widely used hardware: computers and temperature sensors.

There are ways to display the temperature field of a biological object, based on the use of contact temperature sensors connected to computer, where data from the sensors is used for construction of the image of the temperature field of the examined area on computer screen by means of a computer program (for instance, RU 2276965 C2, 27.05.2006; RU 2003127766 A, 20.03.2005; RU 2267982 C2, 20.01.2006). Presence of pathology is detected by the temperature deviation in the examined area of the body of a biological object from the standard value, which is used as the average value, typical for healthy objects or individual norm of the object obtained by averaging indicators of sensors by measuring the temperature at several points of the examined area on the body of the biological object.

The shortcoming of the known methods is connected to the fact that identification of the pathology is done by the displayed on-screen temperature field, which, specialist conducting the survey connects with a examined area only associatively, and consequently, subjective judgment significantly influences on identification of the pathology. Subjective judgment is aggravated by the fact that every biological object has its own specific physical structure. This reduces accuracy and hampers clarity of the examination. Moreover, accuracy of temperature field's reproduction depends on the characteristics of the employed contact thermometers, readings of which, in the given time, are determined by the condition of the skin of a biological object, in particular, by its humidity. This requires preliminary measurement of the dependence of the thermometer's readings on skin's characteristics and input of this dependence in the algorithm of the received data processing. In addition, the readings of a contact thermometer depend on the conditions of the readout procedure, for example, on the extent of pressure of the thermometer on the human body during measurement.

As the nearest analogue to the claimed method was chosen method known RU 2007138079 A, 27.04.2009. The method of displaying of the temperature field of biological object includes temperature measurement of the object by contact temperature sensors in fixed points on the examined area, transfer of measurement results in each fixed point to the computer equipped with a specialized program, processing of measurement results by the computer, and the use of processed measurement results for creation of the image of temperature field of the examined area on the object, which is displayed on the computer screen. The method provides even distribution of contact of the sensors with the surface of the diagnosed area of the body of the biological object, for which purpose the examined area of the body surface of the object is tightly pressed out with an elastic suit. The time for output of the sensors in the steady-state condition is set, and, by using control logic, operative serial interrogation of temperature sensors is performed. The measured temperature values are used to form an array of temperature data, which is transmitted to the computer; the array of data of measured temperature values is formed in the hard memory of the computer. Then, in accordance with a preinstalled computer program, that data is processed and displayed on the screen of the computer.

The disadvantage of this method as well as the methods described above is that the accuracy of displaying of temperature field depends on many parameters, reducing its self-descriptiveness, which results in the presence of significant subjective factor in identifying pathologies. In addition, the use of the resulting image deprives the examination of clarity. Disadvantages also include long duration and complexity of the procedure of measuring temperature because of the need for special measures for elimination of the dependence of the readings of the sensors on the skin condition of a biological object.

SUMMARY OF THE INVENTION

The technical result that is obtained by using the proposed method is to increase the accuracy of generated image of temperature field on the examined area of the object by fixing of the received image of the temperature field to the parameters of the examined area; and to increase the accuracy and clarity of identifying pathologies by using the present invention. The method is easy to implement, and it is carried out with the use of technical tools that are widely used today. In addition, the present invention allows a person to monitor his or her temperature field, save it in the database of the computer, and transmit this data to the appropriate specialist in a medical center for detection of pathologies and their diagnostics.

The technical result is achieved due to the fact that the way of displaying of the temperature field of the biological object (including temperature measurement of the object in the fixed points on the examined area, transfer of measurement result at each fixed point to computer with preinstalled computer program, processing of the results of measurements in the computer, and the use of processed results to form an image of temperature field of the examined area of the object) is characterized by the fact that the image of the examined area of the object is preliminary inputted in the computer database and displayed on the screen, herewith, temperature measurement points on the examined area of the object are displayed on the image of the object on the computer screen, and after making measurements and processing of the results of measurements, the image of temperature field of the examined area of the object is formed on the image of the examined area of the object by the computer program in the computer.

Temperature field of the examined area of the object can be formed in a computer by interpolating the temperatures measured at different points on the examined area of the object.

It is advisable to form the temperature field of the examined area of the object in the computer by linear interpolation of the temperatures measured at adjacent points on the examined area of the object.

The image of the temperature field of the object can be displayed on the computer screen in accordance to the color palette entered into the computer program, in which each temperature value corresponds to a particular color.

It is advisable to measure the temperature by infrared thermometer or infrared pyrometer. For increasing self-descriptiveness, it is appropriate to display the temperature (measured at a specific point of the examined area of the object) in digital form on the computer screen to the corresponding point on the image of the examined area of the object.

The invention is based on the proposal to display the temperature field of the object directly on the image of the examined area of the body of the biological object displayed on the computer screen, and to measure the temperature on the examined area at the points corresponding to the points selected and recorded on the image. When implementing the method, the points for measuring can be either immediately set on the image of the object or set sequentially, after each measurement in the previously selected point. The accuracy of the temperature field formation depends on the number of measurement points and the distances between them: the more points are set with lesser distance between them, the greater the accuracy of the formation of the temperature field.

Herewith, as the image of the examined area is used the electronic image of the examined area of the object received on the photosensitive element of the camera, which can be subsequently transferred to a personal computer in any conventional format, or the image of the examined area on a model of a biological object in 2D or 3D format.

Implementation of the method is carried out by using the computer program, including the algorithms that implement fixation of points for temperature measurement on outputted on computer screen image of the examined area; the results of measurements are reflected on the points, and the temperature distribution in a form of a thermogram is formed directly on the image of the examined area, that is receive the same image as the image of thermal radiation in thermography.

Different algorithms can be used for the formation of the temperature field of the object on the computer screen, however, rather simple and informative is the algorithm based on the interpolation of the measured temperatures at adjacent points for determining the temperature values between these points, herewith, the most simple algorithm is built on the principle of linear interpolation. The algorithm includes the step of constructing the convex surface based on the measured array of points that correspond to the points of temperature measurement, and the partition (triangulation) of the constructed surface to the sectors in the form of polygons, the angles of which coincide with the points of temperature measurements. Further, the algorithm provides determination of the temperature between the adjacent points by interpolation method, determination of the angles of inclination of each polygon, and formation of the bit image data of the temperature field, which is superimposed on the image of the examined object.

The used algorithm also allows displaying the temperature measured at a specific point of the examined area of the object in a digital form on the screen in the corresponding point on the image of the examined object. Output of the temperatures measured in numerical terms increases the information content of the proposed method.

The color palette is used for visualization of the temperature field; in the color palette, certain temperature corresponds to certain color. The algorithm of the computer program fills every pixel of the processed image of the temperature field in the appropriate color.

To display the temperature field of the object, contact as well as infrared (non-contact) thermometer or pyrometer can be used for temperature measurement of a biological object, however, the use of an infrared thermometer or pyrometer is preferred in virtue of the above described shortcomings of contact thermometers.

The use of the photographic image of the examined area of the object that is intrinsic to the specific object increases the accuracy of displaying the temperature field and excludes the impact of anatomical (physical) structure of the biological object on locating pathology in the body of the biological object. Visualization and increase of efficiency of identifying a wide range of pathological processes that can develop in humans and animals is achieved due to this technique. In addition, the claimed method allows visual assessment of the effectiveness of treatment of diseases. Using the proposed method allows to assess the effectiveness of each treatment procedure.

DESCRIPTION OF THE PREFERRED EMBODIMENTS

Figure 1:
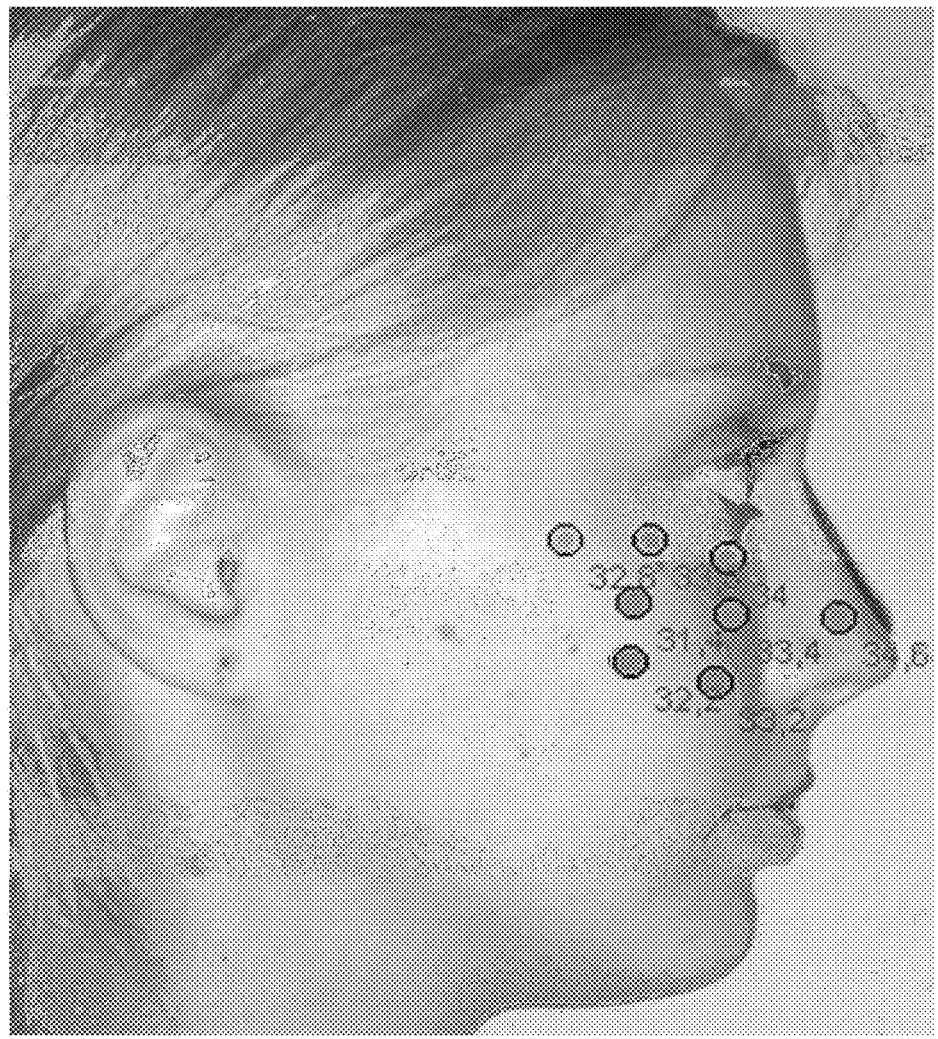
FIG. 1 is a photographic image of the face of an individual, on which temperature measurement points are marked.
Figure 2:
FIG. 2 is the image of the temperature field, formed on the base of the temperatures measured at the points shown in the photographic image the person shown on FIG. 1.
Figure 3:
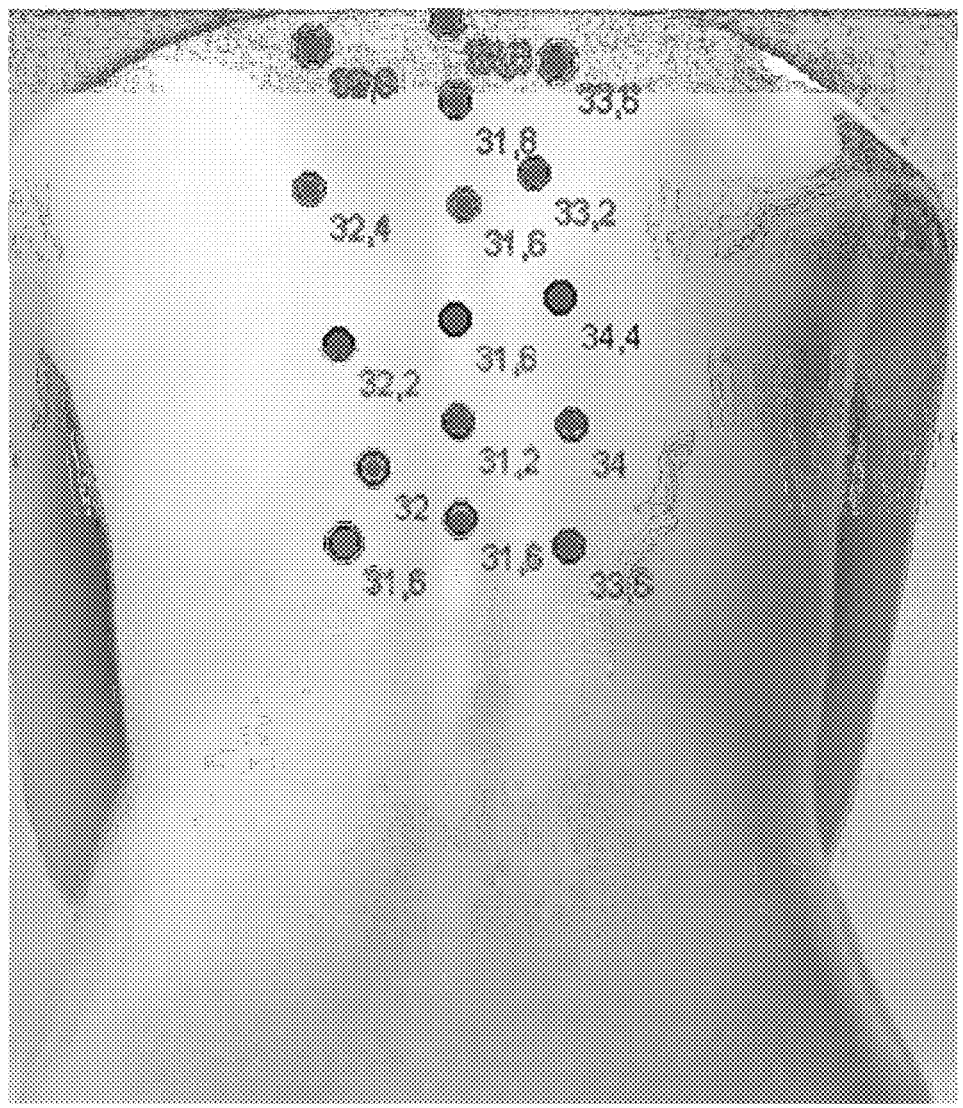
FIG. 3 is a photographic image of the back of an individual, on which temperature measurement points are marked.
Figure 4:
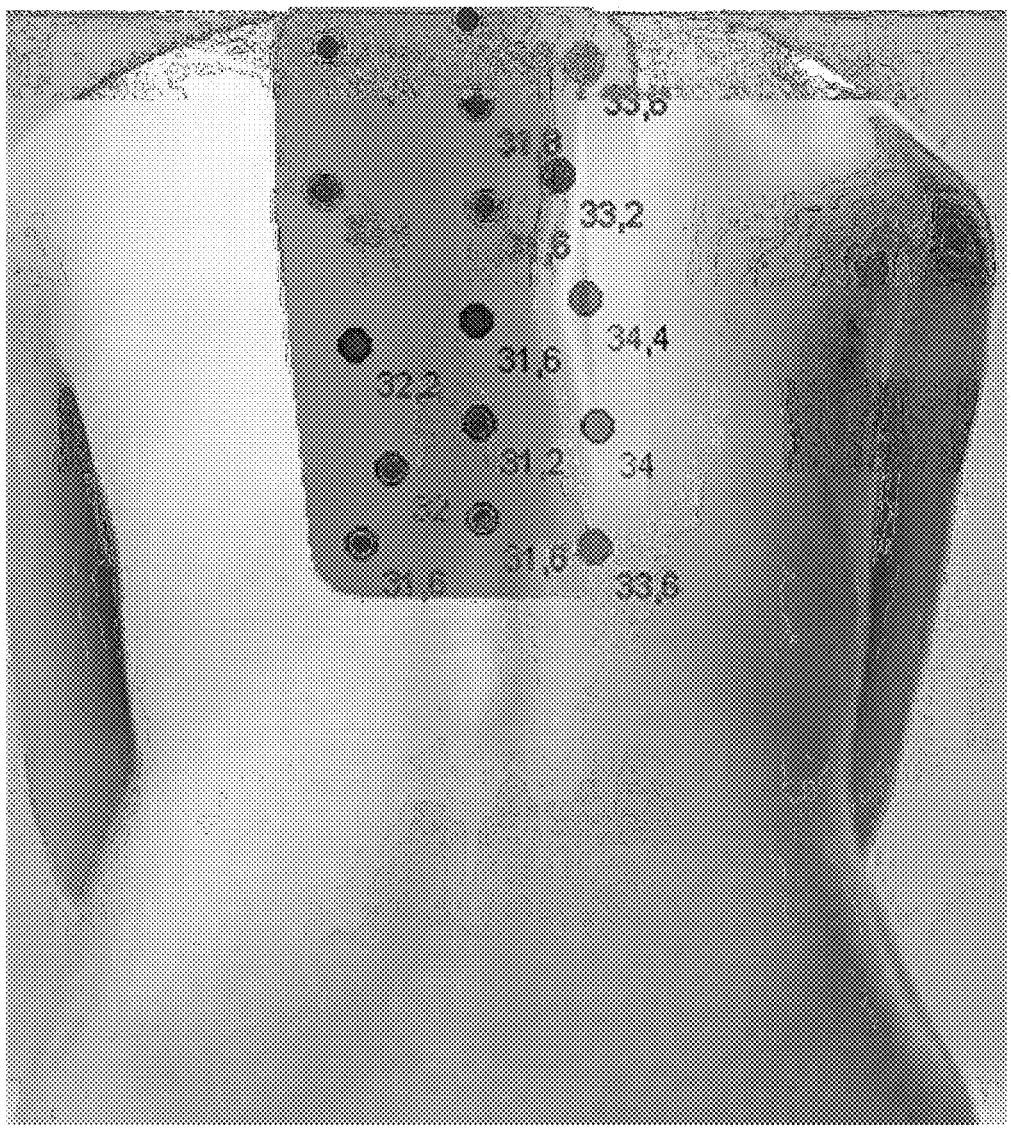
FIG. 4 is an image of the temperature field, constructed based on the temperatures measured at the points indicated on the photographic image of the back shown on FIG. 3.

An example of implementation of the claimed method is described below.

First, pictures of an examined area are taken by photographic camera that has means for entering the photos into the database of the computer equipped with the program ensuring the algorithm of processing of the inputted data in the computer in accordance with the claimed method. The photo of the examined area of the biological object is displayed on the computer screen.

Points for temperature measurement are fixed on the image of the examined area of the biological object on the computer screen, then, by infrared thermometer, the temperature is consistently measured on the examined area at the points corresponding to the location of the points on the image of the object. The measurement results are transmitted to the computer, in which the measured data is processed and displayed on the screen to the corresponding point on the image of the surveyed area of the body of the biological object.

The received data of temperature measurements is outputted by the computer program to the screen in the form of thermogram that is superimposed on a photographic image of the examined area of the biological object.

The method has been tested and used to detect inflammatory, vascular, and tumor pathologies in humans and animals.

The invention claimed is:

1. A method for displaying a temperature field of an area of a human skin surface in order to monitor a pathological process, comprising:
    saving a digital image of the area of the human skin surface in a memory of a computer and displaying the digital image on a computer screen; the digital image acquired using a camera;
    marking pre-measurement points on the digital image displayed on the computer screen, the pre-measurement points corresponding to points on the area of the human skin surface;
    measuring, using one of an infrared thermometer and an infrared pyrometer, the temperature only at the points of the human skin surface corresponding to the pre-measurement points previously marked on the digital image;
    providing measured values of the temperature at said points of the human skin surface corresponding to the pre-measurement points previously marked on the digital image to the computer;
    generating a temperature field using only the measured values of temperatures and the computer that is configured to generate the temperature field; since temperature is measured at said points corresponding to the pre-measurement points marked on the digital image, the temperature field is formed superimposed on the digital image;
    saving an image of the temperature field superimposed on the digital image of the area of the human skin surface in the computer; and
    displaying the image of the temperature field superimposed on the digital image of the area of the human skin surface on the computer screen;
    whereby displaying a temperature field of an area of a human skin surface is used to detect inflammatory, vascular, and tumor pathologies in humans.

2. The method of claim 1, wherein the temperature field of the area of the human skin surface is formed by interpolation of temperatures, measured at the pre-measurement points.

3. The method of claim 2, wherein the temperature field of the area of the human skin surface is formed by linear interpolation of temperatures, measured in adjacent pre-measurement points on the area of the human skin surface.

4. The method of claim 2, wherein the image of the temperature field of the area of the human skin surface is displayed on the computer screen in accordance with a computer program color palette, in which each specific color corresponds to a temperature value.

5. The method of claim 2 further comprising displaying the image of the temperature field on the computer screen.

6. The method of claim 1, wherein the measured values of the temperature are displayed in a numerical form on the screen of the computer at corresponding pre-measurement points on the image of the area of the human skin surface.

7. The method of claim 1, wherein temperature measurements are obtained serially.

8. The method of claim 1 further comprising saving the temperature field in a database.

* * * * *